(12) United States Patent
Schaefer et al.

(10) Patent No.: US 12,011,263 B2
(45) Date of Patent: Jun. 18, 2024

(54) INTEGRATED OPTICAL FILTER SYSTEM WITH LOW SENSITIVITY TO HIGH ANGLE OF INCIDENCE LIGHT FOR AN ANALYTE SENSOR

(71) Applicant: Senseonics, Incorporated, Germantown, MD (US)

(72) Inventors: Joshua C. Schaefer, Germantown, MD (US); Andrew DeHennis, Germantown, MD (US); Szymon Tankiewicz, Germantown, MD (US)

(73) Assignee: Senseonics, Incorporated, Germantown, MD (US)

( * ) Notice: Subject to any disclaimer, the term of this patent is extended or adjusted under 35 U.S.C. 154(b) by 665 days.

(21) Appl. No.: 17/188,817

(22) Filed: Mar. 1, 2021

(65) Prior Publication Data

US 2021/0177311 A1    Jun. 17, 2021

Related U.S. Application Data

(63) Continuation of application No. 16/698,041, filed on Nov. 27, 2019, now Pat. No. 10,932,703, which is a
(Continued)

(51) Int. Cl.
*A61B 5/1455* (2006.01)
*A61B 5/145* (2006.01)
*A61B 5/1459* (2006.01)

(52) U.S. Cl.
CPC ........ *A61B 5/1455* (2013.01); *A61B 5/14532* (2013.01); *A61B 5/1459* (2013.01); *A61B 2562/0233* (2013.01)

(58) Field of Classification Search
CPC ....... G01N 21/6428; G01N 2021/7786; G01N 21/64; G01N 21/77; G01N 2021/7783;
(Continued)

(56) References Cited

U.S. PATENT DOCUMENTS 5,999,321 A    12/1999  Bradley
8,233,953 B2    7/2012  Colvin, Jr.
(Continued)

FOREIGN PATENT DOCUMENTS

CN    102981199 A    3/2013
EP    2 746 738 A2    6/2014
(Continued)

OTHER PUBLICATIONS

Romain Girard-Desprolet et al., "Angular and polarization properties of cross-holes nanostructured metallic filters," Optics Express, vol. 21, No. 24, p. 29412, XP055428188, DOI: 10.1364/OE.21.029412, 13 pages (Nov. 21, 2013).
(Continued)

*Primary Examiner* — Balram T Parbadia
(74) *Attorney, Agent, or Firm* — Rothwell, Figg, Ernst & Manbeck, P.C.

(57) ABSTRACT

Apparatuses and methods for improving the accuracy of an analyte sensor are disclosed. The sensor may include a photodetector and a low angle sensitive (LAS) optical filter. The photodetector may be configured to convert received light into current indicative of the intensity of the received light. The LAS optical filter may be configured to prevent light having a wavelength outside a band pass region from reaching the photodetector and to pass light having a wavelength within the band pass region to the photodetector. The percentage of light passing through the LAS optical filter may decrease as the angle of incidence of the light increases.

28 Claims, 8 Drawing Sheets
(5 of 8 Drawing Sheet(s) Filed in Color)

Related U.S. Application Data continuation of application No. 14/799,979, filed on Jul. 15, 2015, now Pat. No. 10,537,269.

(60) Provisional application No. 62/024,595, filed on Jul. 15, 2014.

(58) Field of Classification Search
CPC ... G01N 21/552; G01N 21/648; G01J 1/0488; G01J 1/42; G01J 3/0256; G01J 1/0214; G01J 1/06; G01J 1/1626; G01J 2003/1226; G01J 3/4406; G01J 2003/1213; G02B 5/283; G02B 5/208; G02B 5/285; G02B 5/008; G02B 5/08; G02B 5/20; F21V 9/04; F21V 9/06; A61B 5/1455; A61B 5/14532; A61B 2562/0233; A61B 5/1459
See application file for complete search history.

(56) References Cited

U.S. PATENT DOCUMENTS

| | | |
|---|---|---|
| 8,746,888 B2 | 6/2014 | Silverstein |
| 9,135,891 B2 | 9/2015 | Seo et al. |
| 9,151,956 B2 | 10/2015 | Huang |
| 9,414,775 B2 | 8/2016 | Colvin, Jr. et al. |
| 9,693,714 B2 | 7/2017 | DeHennis et al. |
| 2005/0035304 A1 | 2/2005 | Colvin, Jr. et al. |
| 2006/0231749 A1 | 10/2006 | Colvin et al. |
| 2013/0181973 A1 | 7/2013 | Silverstein |
| 2013/0182226 A1 | 7/2013 | Silverstein |
| 2013/0182320 A1 | 7/2013 | Silverstein |
| 2013/0182321 A1 | 7/2013 | Silverstein |
| 2013/0211213 A1 | 8/2013 | DeHennis et al. |
| 2013/0241745 A1 | 9/2013 | Colvin, Jr. et al. |
| 2013/0324819 A1 | 12/2013 | Colvin, Jr. |
| 2014/0168742 A1 | 6/2014 | Hashimura et al. |
| 2014/0168761 A1 | 6/2014 | Ockenfuss |
| 2014/0170765 A1 | 6/2014 | Ockenfuss |
| 2016/0015302 A1 | 1/2016 | Schaefer |
| 2017/0191870 A1 | 7/2017 | Ockenfuss |

FOREIGN PATENT DOCUMENTS

| | | |
|---|---|---|
| EP | 2 746 739 A2 | 6/2014 |
| WO | 2013/163298 A1 | 10/2013 |
| WO | 2014/014930 A2 | 1/2014 |

OTHER PUBLICATIONS

Marc Dandin et al., "Optical filtering technologies for integrated fluorescence sensors," Lab on a Chip. vol. 7, No. 8, pp. 955-977, XP055428261, ISSN: 1473-0197, DOI: 10.1039/b704008c (Jan. 1, 2007).

Vivek Raj Shrestha et al., "Non-iridescent Transmissive Structural Color Filter Featuring Highly Efficient Transmission and High Excitation Purity," Scientific Reports, vol. 4, No. 1, XP055428165, DOI: 10.1038/srep04921, 8 pages (May 12, 2014).

Jin-long Zhang et al., "Omnidirectional narrow bandpass filter based on metal-dielectric thin films," Applied Optics, vol. 47, No. 33, pp. 6285-6290, XP055428313, ISSN: 0003-6935, DOI: 10.1364/AO.47.006285 (Nov. 20, 2008).

Stephan Junger et al., "On-chip nanostructures for polarization imaging and multispectral sensing using dedicated layers of modified CMOS processes," Photonic and Phononic Properties of Engineered Nanostructures, SPIE, vol. 7946, No. 1, pp. 1-7, XP060007731, DOI: 10.1117/12.874785 (Feb. 10, 2011).

Jing Zhou et al., "Transition from a spectrum filter to a polarizer in a metallic nano-slit array," Scientific Reports, vol. 4, No. 1, XP055428178, DOI: 10.1038/srep03614 (Jan. 9, 2014).

INTEGRATED OPTICAL FILTER SYSTEM WITH LOW SENSITIVITY TO HIGH ANGLE OF INCIDENCE LIGHT FOR AN ANALYTE SENSOR

CROSS-REFERENCE TO RELATED APPLICATION

The present application is a continuation of U.S. patent application Ser. No. 16/698,041, filed on Nov. 27, 2019, which is a continuation of U.S. patent application Ser. No. 14/799,979, filed on Jul. 15, 2015, which claims the benefit of priority to U.S. Provisional Application Ser. No. 62/024,595, filed on Jul. 15, 2014, which are incorporated herein by reference in their entireties.

BACKGROUND

Field of Invention

The present invention relates generally to an optical filtering system in a sensor configured to detect an analyte within a medium within a living animal. The present invention also relates to an optical filtering system having low sensitivity to high angle of incidence light.

Discussion of the Background

A sensor may be implanted within a living animal to measure an analyte in a medium within the living animal. Examples of implantable sensors employing an analyte indicator to measure an analyte are described in U.S. Pat. No. 8,233,953 and U.S. Patent Application Publication Nos. 2013/0211213, 2013/0241745, and 2013/0324819, all of which are incorporated by reference in their entireties.

FIG. 1 illustrates a cross-sectional view of an example of an existing sensor 100. FIG. 2 illustrates a cross-sectional view of the existing sensor 100 in operation. FIG. 3 is a schematic view of the existing sensor 100. FIG. 4 illustrates various sources of light in the optical system of the optical system of the existing sensor 100. The sensor 100 includes a light source 108 that emits excitation light 129 (e.g., at an excitation wavelength of 378 nm) to an analyte indicator 106 (e.g., a polymer graft) containing indicator molecules 104 (see FIG. 3). The indicator molecules 104 have an optical characteristic that varies based on the concentration of the analyte in the medium. In particular, when excited by the excitation light 129, indicator molecules 104 that have bound the analyte emit (i.e., fluoresce) light 131 having a wavelength different than the wavelength of the excitation light 129 (e.g., the emission light 131 may have a wavelength range of about 400 nm to 500 nm with a peak emission wavelength around 435 nm) (see FIG. 4). Higher analyte levels correspond to a greater amount of emission light 131 of the indicator molecules 104 in the analyte indicator 106, and, therefore, a greater amount of photons striking a first photodetector (e.g., photodiode) 110.

The sensor 100 includes a first dichroic band pass filter 111 (thin film) that filters light incident on the first photodetector 110. The first dichroic band pass filter 111 is designed to only pass light having the wavelength of the light emitted by the indicator molecules 104 (e.g., light within the range of about 400 nm to 500 nm) so that, in theory, the first photodectector 110, which is a signal photodetector, only receives the light emitted by the indicator molecules 104.

In sensors having multiple channels (e.g., a signal channel and a reference channel) and/or multiple photodiodes, the sensor may include a dichroic band pass filter for each channel and/or photodetector. For instance, as shown in FIGS. 1-3, existing sensor 100 includes a second dichroic band pass filter 113 (thin film) that filters light incident on a second photodetector 112. The second dichroic band pass filter 113 is designed to only pass light having the wavelength of reference light so that, in theory, the second photodectector 112, which is a reference photodetector, only receives the reference light. In the existing sensor 100, the first photodectector 110 and the second photodetector 112 are arranged symmetrically on either side of the light source 108.

In the existing sensor 100, the dichroic band pass filter 111 is coated onto a glass slide 220, which is then attached to the photodetector 110, and the dichroic band pass filter 113 is coated onto a glass slide 222, which is then attached to the photodetector 112. In existing sensor 100, light (e.g., reflected excitation light 129 and fluorescent light 131 emitted by the indicator molecules 104 in the analyte indicator 106) passes through one or more glass slides 220 and 222.

The existing sensor 100 includes a sensor housing 102 (i.e., body, shell, capsule, or encasement), which may be rigid and biocompatible. The sensor housing 102 is formed from a suitable, optically transmissive polymer material (e.g., epoxy), such as, for example, acrylic polymers (e.g., polymethylmethacrylate (PMMA)). The sensor housing 102 may be any shape suitable for implantation into a living animal. The existing sensor 100 includes a substrate 116 and an encoder 118 that encodes the data before it is conveyed to an external transceiver.

In practice, the dichroic filters 111 and 112 allow the passage of light that was not intended to pass through, which may degrade the accuracy of the sensor. Accordingly, there is a need for sensors having improved accuracy and in which these problems are substantially reduced or eliminated.

SUMMARY

The present invention overcomes the disadvantages of prior systems by providing, among other advantages, a low angle sensitive (LAS) optical filter to reduce the transmission of light having high angles of incidence to the photodetector. That is, the LAS optical filter may have a transmission efficiency that is dependent on angle of incidence such that the transmission efficiency of the LAS optical filter decreases as the angle of incidence increases. In addition, the LAS optical filter may be configured to prevent light having a wavelength outside a band pass region from reaching the photodetector and to pass light having a wavelength within the band pass region to the photodetector.

One aspect of the invention may provide a sensor for measurement of an analyte in a medium within a living animal. The sensor may include a photodetector and a low angle sensitive (LAS) optical filter. The photodetector may be configured to convert received light into current indicative of the intensity of the received light. The LAS optical filter may be configured to prevent light having a wavelength outside a band pass region from reaching the photodetector and to pass light having a wavelength within the band pass region to the photodetector. The percentage of light passing through the LAS optical filter may decrease as the angle of incidence of the light increases.

Another aspect of the invention may provide a method of detecting an analyte using a sensor. The sensor may comprise a light source, an analyte indicator, a low angle sensitive (LAS) optical filter having low sensitivity to high angle incidence light, and a photodetector. The method may include irradiating, by the light source, excitation light to the analyte indicator. The method may include emitting, by the analyte indicator, emission light to the LAS optical filter. The method may include receiving, by the LAS optical filter, light including emission light emitted by the analyte indicator. The method may include preventing, by the LAS optical filter, light of the received light having one or more of a wavelength outside a band pass region and a high angle of incidence from reaching the photodetector. The method may include passing, by the LAS optical filter, light of the received light having a wavelength within the band pass region to the photodetector. The percentage of light passed by the LAS optical filter may decrease as the angle of incidence of the light increases. The method may include receiving, by the photodetector, the passed light.

Another aspect of the invention may provide a method of manufacturing an analyte sensor. The method may include fabricating or mounting a photodetector in or on a substrate and forming a low angle sensitive (LAS) optical filter by depositing layers of metal and oxides on the photodetector. The LAS optical filter may be configured to prevent light having a wavelength outside a band pass region from reaching the photodetector and to pass light having a wavelength within the band pass region to the photodetector. The percentage of light passed through the LAS optical filter may decrease as the angle of incidence of the light increases.

Further variations encompassed within the sensors, systems and methods are described in the detailed description of the invention below.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The accompanying drawings, which are incorporated herein and form part of the specification, illustrate various, non-limiting embodiments of the present invention. In the drawings, like reference numbers indicate identical or functionally similar elements.

DETAILED DESCRIPTION OF PREFERRED EMBODIMENTS

Figure 9:
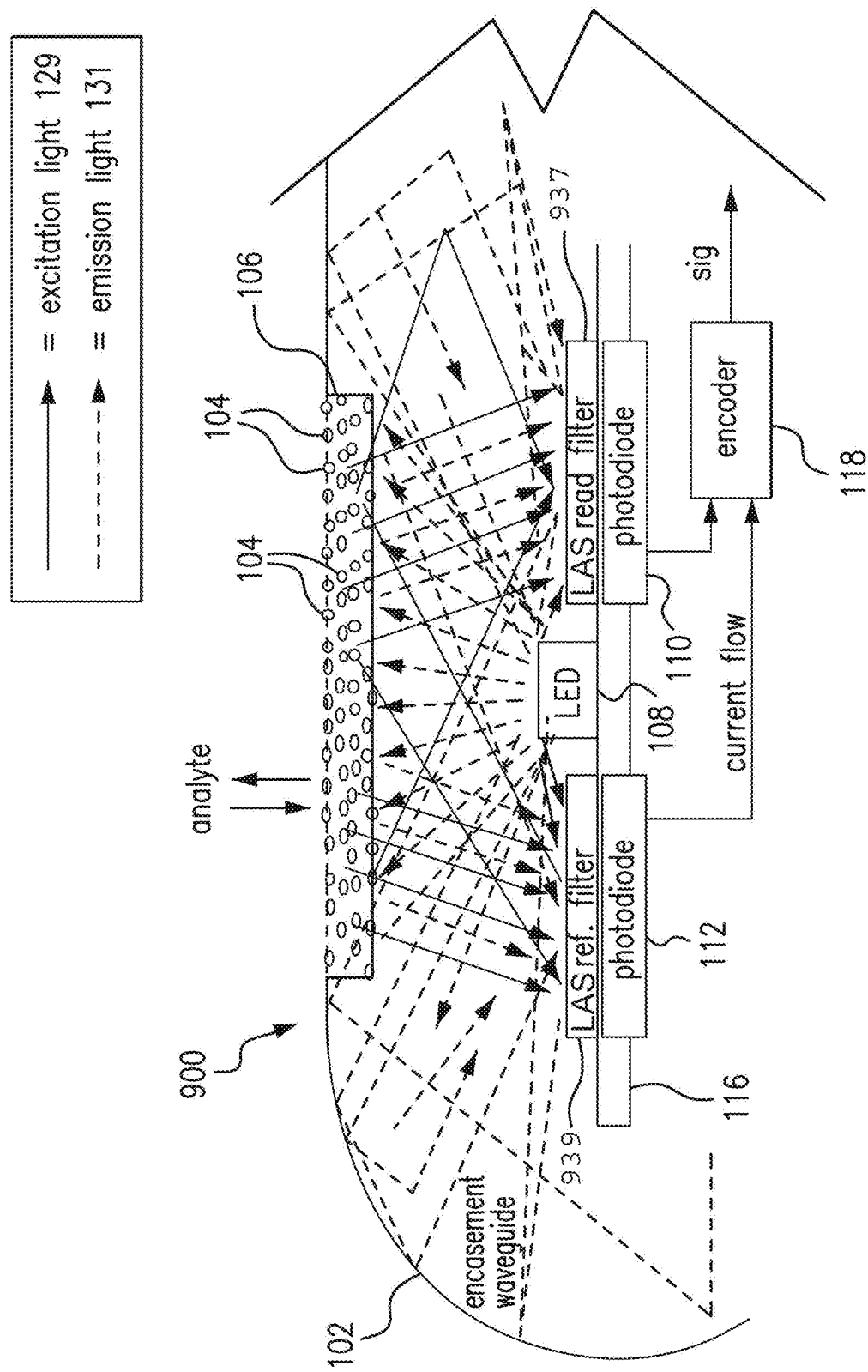
FIG. 9 is a schematic view of a sensor embodying aspects of the present invention.

FIG. 9 is a schematic view of a sensor 900 embodying aspects of the present invention. In some non-limiting embodiments, the sensor may be part of an analyte monitoring system. The system may include the sensor and an external transceiver. In some non-limiting embodiments, the sensor may be a fully implantable continuous analyte (e.g., glucose, oxygen, cardiac markers, low-density lipoprotein (LDL), high-density lipoprotein (HDL), or triglycerides) monitoring sensor. The sensor may be implanted in a living animal (e.g., a living human) and may wirelessly communicate with the external transceiver (e.g., via an inductive magnetic link). The sensor may be implanted, for example, in a living animal's arm, wrist, leg, abdomen, peritoneum, intravenously, or other region of the living animal suitable for sensor implantation. For example, in one non-limiting embodiment, the analyte sensor may be implanted beneath the skin (e.g., in the subcutaneous or peritoneal tissues), and no portion of the sensor protrudes from the skin. Although, in some embodiments, the sensor may be a fully implantable sensor, this is not required, and, in some alternative embodiments, the analyte sensor may be a transcutaneous sensor having a wired connection to an external transceiver. For example, in some alternative embodiments, the analyte sensor may be located in or on a transcutaneous needle (e.g., at the tip thereof). In some embodiments, the analyte sensor may be an optical sensor (e.g., a fluorometer). In some embodiments, the analyte sensor may be a chemical or biochemical sensor. In a non-limiting embodiment, the sensor 900 may be a highly miniaturized dual channel precision fixed wavelength fluorimeter. In some non-limiting embodiments, the analyte sensor may be capable of being continuously implanted for at least 90 days or longer and may be replaced thereafter.

Figure 5:
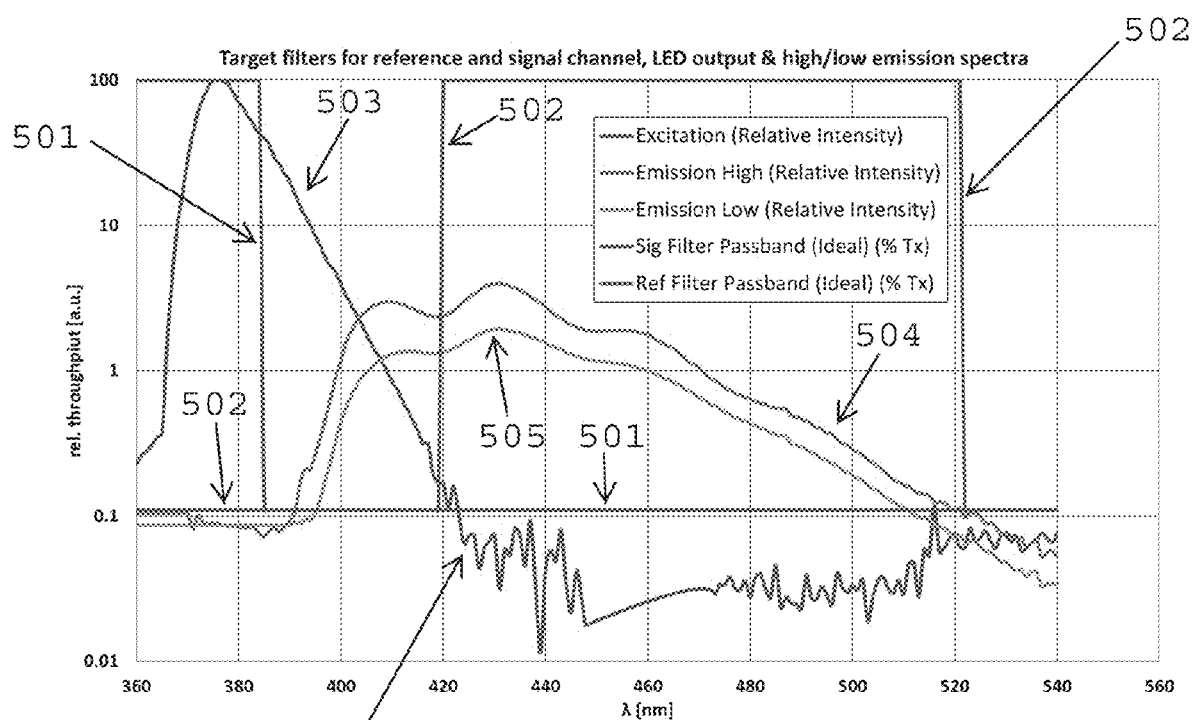
FIG. 5 is a graph illustrating ideal signal and reference filter passbands, the spectrum of excitation light emitted by the light source, and the spectra of high and low emissions of indicator molecules of the analyte indicator.

In some non-limiting embodiments, as illustrated in FIG. 9, the sensor 900 may be encased in a sensor housing 102 (i.e., body, shell, capsule, or encasement), which may be rigid and biocompatible. The sensor 900 may include an analyte indicator 106, such as, for example, a polymer graft coated, diffused, adhered, or embedded on or in at least a portion of the exterior surface of the sensor housing 102. The analyte indicator 106 (e.g., polymer graft) of the sensor 900 may include indicator molecules 104 (e.g., fluorescent indicator molecules) exhibiting one or more detectable properties (e.g., optical properties) based on the amount or concentration of the analyte in proximity to the analyte indicator element. In some embodiments, the sensor 900 may include a light source 108 that emits excitation light 129 over a range of wavelengths that interact with the indicator molecules 104. The sensor 900 may also include one or more photodetectors 110, 112 (e.g., photodiodes, phototransistors, photoresistors, or other photosensitive elements). The one or more photodetectors (e.g., photodetector 110) may be sensitive to emission light 131 (e.g., fluorescent light) emitted by the indicator molecules 104 such that a signal generated by a photodetector (e.g., photodetector 110) in response thereto that is indicative of the level of emission light 131 of the indicator molecules and, thus, the amount of analyte of interest (e.g., glucose). In some non-limiting embodiments, one or more of the photodetectors (e.g., photodetector 112) may be sensitive to excitation light 129 that is reflected from the analyte indicator 106. In one non-limiting embodiment, the excitation light 329 may have a wavelength of approximately 378 nm, and the emission light 331 may have a wavelength in the range of 400 to 500 nm with a peak emission around 435 nm, as shown in FIG. 5. However, this is not required, and, in some alternative embodiments, the excitation light 329 and/or emission light 131 have different wavelengths.

In some embodiments, as illustrated in FIG. 9, the sensor 900 may include a substrate 116. In some embodiments, the substrate 116 may be a circuit board (e.g., a printed circuit board (PCB) or flexible PCB) on which circuit components (e.g., analog and/or digital circuit components) may be mounted or otherwise attached. However, in some alternative embodiments, the substrate 116 may be a semiconductor substrate having circuitry fabricated therein. The circuitry may include analog and/or digital circuitry. Also, in some semiconductor substrate embodiments, in addition to the circuitry fabricated in the semiconductor substrate, circuitry may be mounted or otherwise attached to the semiconductor substrate 116. In other words, in some semiconductor substrate embodiments, a portion or all of the circuitry, which may include discrete circuit elements, an integrated circuit (e.g., an application specific integrated circuit (ASIC)) and/or other electronic components (e.g., a non-volatile memory), may be fabricated in the semiconductor substrate 116 with the remainder of the circuitry is secured to the semiconductor substrate 116, which may provide communication paths between the various secured components.

In some embodiments, one or more of the sensor 900, sensor housing 102, analyte indicator 106, indicator molecules 104, light source 108, photodetectors 110 and 112, and substrate 116 may include some or all of the structural and/or functional features described in one or more of U.S. application Ser. No. 13/761,839, filed on Feb. 7, 2013, U.S. application Ser. No. 13/937,871, filed on Jul. 9, 2013, and U.S. application Ser. No. 13/650,016, filed on Oct. 11, 2012, all of which are incorporated by reference in their entireties.

In some embodiments, light may have to pass through one or more low angle sensitive (LAS) optical filters before reaching the one or more photodetectors. The LAS optical filters may be configured to allow specific wavelengths of light to pass. In some non-limiting embodiments, as shown in FIG. 9, the sensor 900 may include a signal channel LAS optical filter 937, and light may have to pass through the signal channel LAS optical filter 937 before reaching the signal channel photodetector 110. In some non-limiting embodiments, the sensor 900 may include reference channel LAS optical filter 939, and light may have to pass through the reference channel LAS optical filter 939 before reaching the reference channel photodetector 112.

The signal channel LAS optical filter 937 may be configured to pass a narrow band of wavelengths including the wavelength of the emission light 131 emitted (e.g., fluoresced) by the indicator molecules 104 in the analyte indicator 106. For instance, in embodiments where the peak emission of the indicator molecules 104 occurs around 435 nm, the signal channel LAS optical filter 937 may be configured to pass light in the range of 400-500 nm and prevent other light from reaching the first photodetector 110 (e.g., by reflecting or absorbing most of the light outside the 400-500 nm range). However, this is not required, and, in other sensors 900, the emission light 131 may have a different peak emission wavelength and/or the signal channel LAS optical filter 937 may pass light in a different (e.g., narrower, expanded, or shifted) wavelength range.

The reference channel LAS optical filter 939 may be configured to pass a narrow band of wavelengths including the wavelength of a reference light. In one non-limiting embodiment, the reference light passed by the reference channel LAS optical filter 939 may have the same wavelength as the excitation light 129 (e.g., 378 nm), and the reference channel LAS optical filter 939 may pass light in a narrow band (e.g., 350-400 nm) including the wavelength of the excitation light 129 and prevent other light from reaching the reference photodetector 112. However, this is not required, and, in other embodiments, the reference light passed by the reference channel LAS optical filter 939 may have a different wavelength than the excitation light 129 (e.g., the wavelength of light emitted by reference indicator molecules that are unaffected or generally unaffected by the presence and/or concentration of the analyte), and/or the reference channel LAS optical filter 939 may pass light in a different (e.g., narrower, expanded, or shifted) wavelength range.

In some embodiments, the one or more LAS optical filters may utilize both dichroic and absorptive filtering to greatly reduce the angle sensitivity relative to a conventional dichroic filter (e.g., dichroic filters 111 and 113) configured to allow the specific wavelengths of light to pass. In some embodiments, an LAS optical filter may have a thickness corresponding to the wavelength range (i.e., spectrum) that the LAS optical filter is configured to pass. In some non-limiting embodiments, the one or more LAS optical filters may be ultrathin (e.g., less than or equal to 800 nm thick) layers of metals and/or metal oxides (e.g., tantalum, silver and/or zinc) deposited onto a glass slide or directly onto a photodetector (e.g., photodetector 110 or 112), which may be fabricated in the semiconductor substrate 116. However, this is not required, and, in alternative embodiments, the one or more LAS optical filters may have different thicknesses. In some non-limiting embodiments, the one or more LAS optical filters may be plasmonic nanostructured filters.

Figure 1:
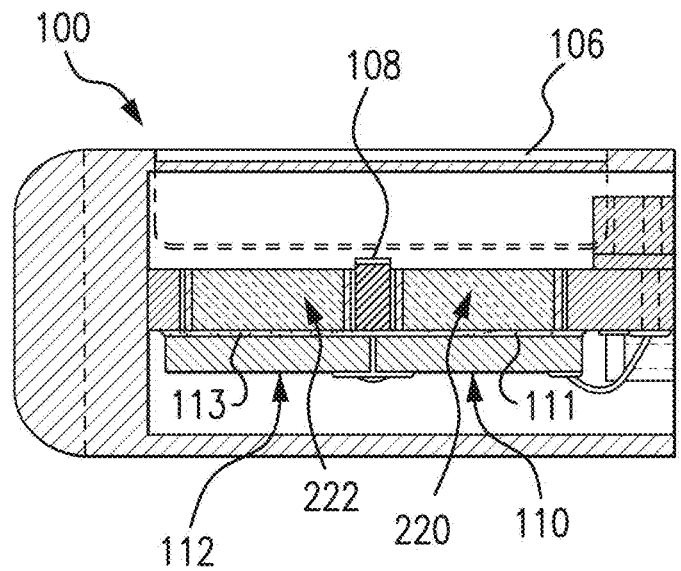
FIG. 1 is a cross-sectional view of an example of an existing sensor.
Figure 2:
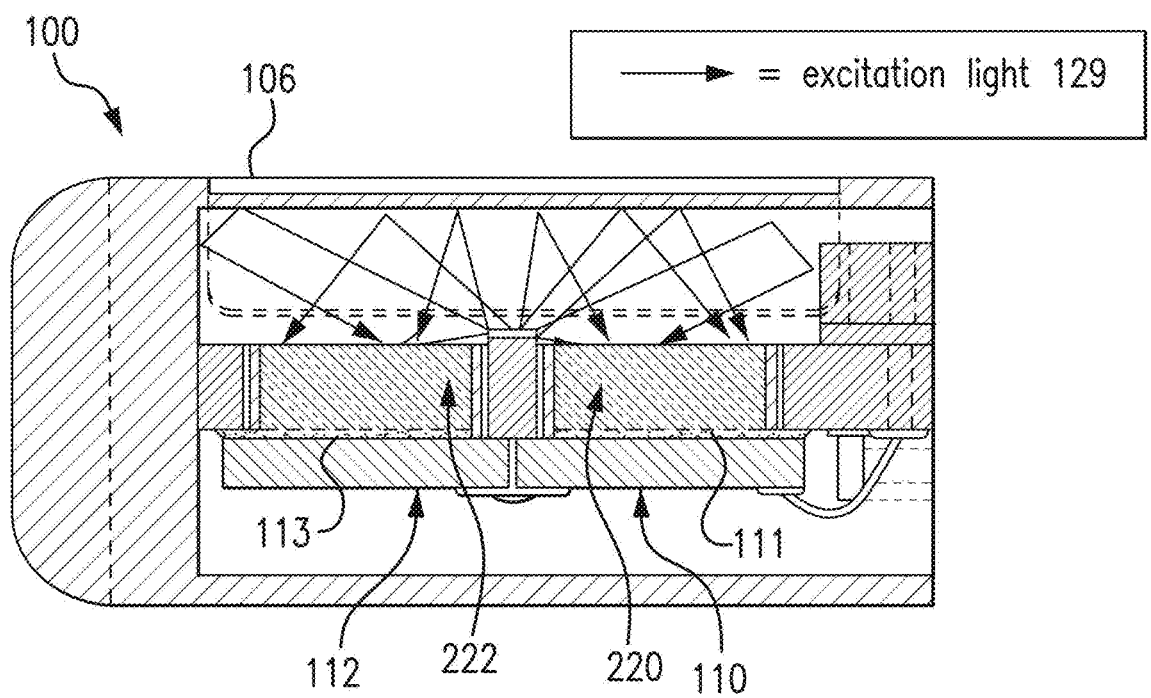
FIG. 2 is a cross-sectional view of the example of an existing sensor in operation.
Figure 3:
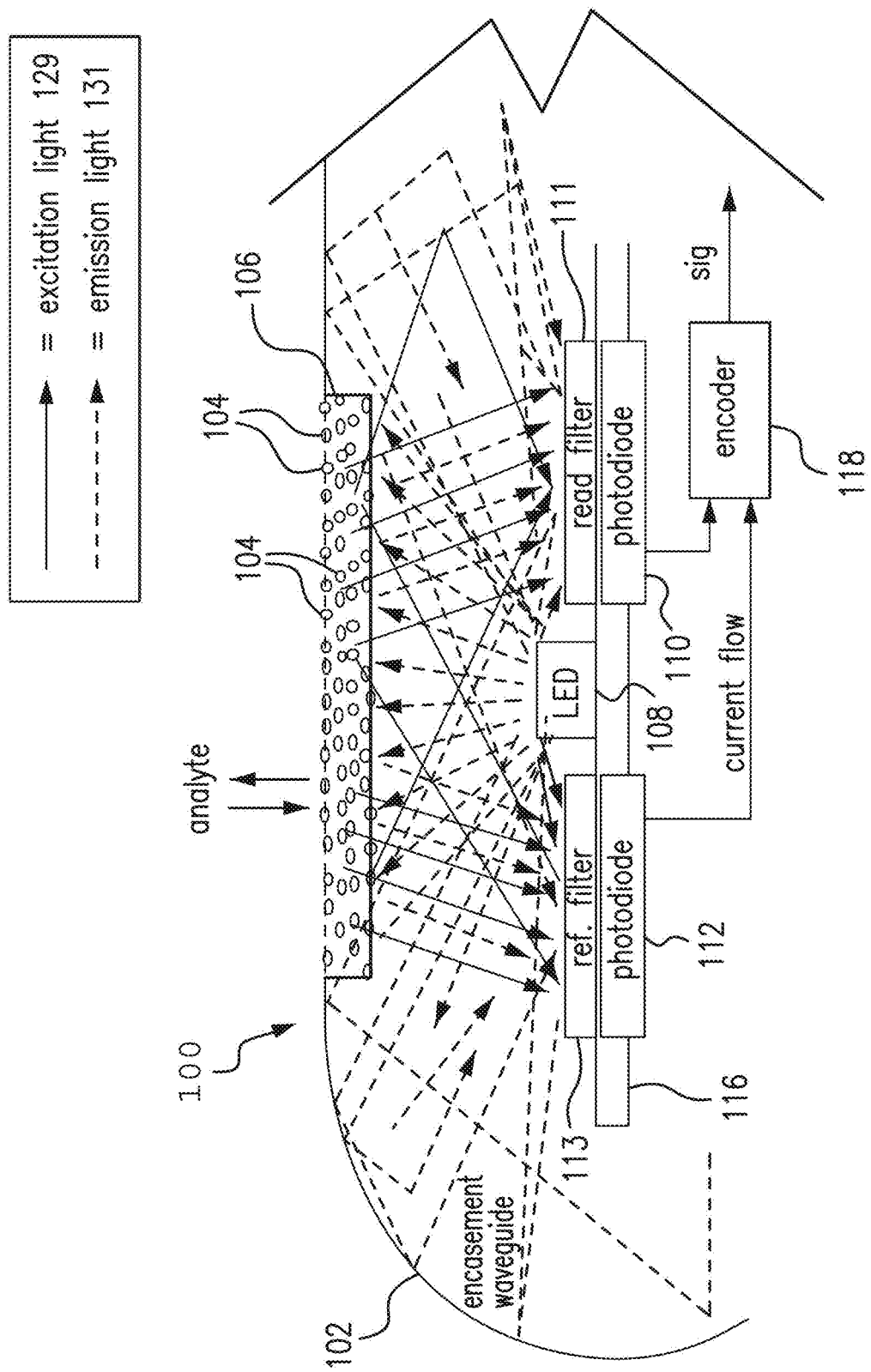
FIG. 3 is a schematic view of an existing sensor.
Figure 4:
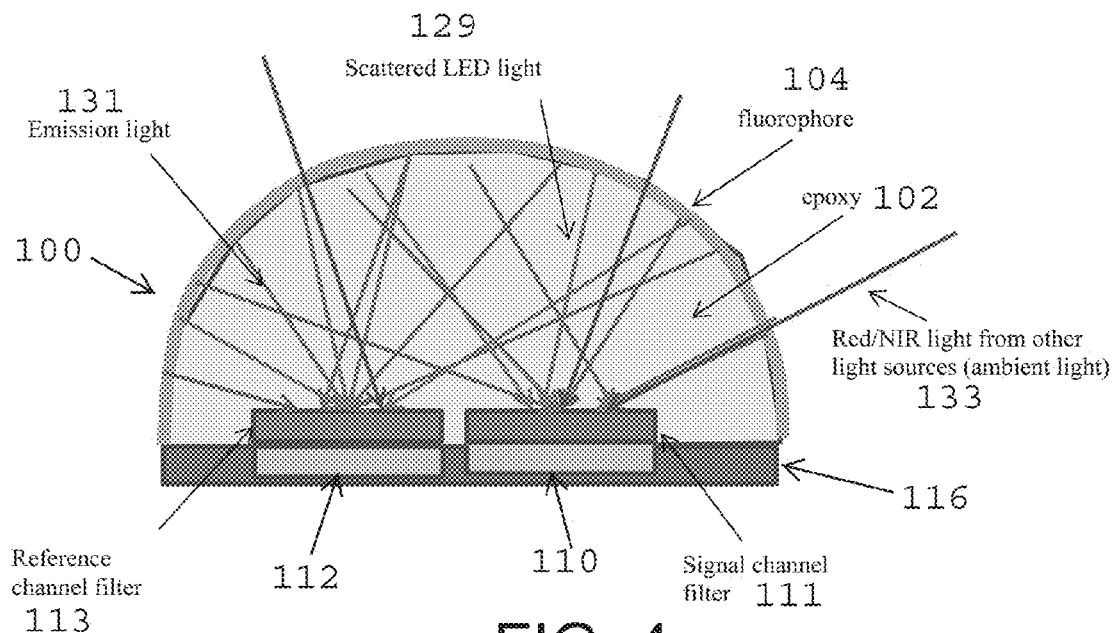
FIG. 4 illustrates various sources of light in the optical system of the optical system of the existing sensor 100.

The conventional dichroic filter technology of dichroic filters 111 and 113 (see FIGS. 1-3) works well at 0-15° angle of incidence, but, at higher angles of incidence, the conventional dichroic filters 111 and 113 begin to shift to lower wavelengths and allow through light that was not intended to pass. As a result, the dichroic band pass filter 111 begins to allow more excitation light 129 to pass through, and the signal channel photodetector 110 begins to capture more excitation light 129. The dichroic band pass filter 111 also begins to allow infrared light 133 (see FIG. 4), which can pass through the skin and into our optical system, to pass through the filter 111 and be captured by the signal channel photodetector 110. As illustrated in FIG. 4, the dichroic filters 111 and 113 and photodetectors 110 and 112 are subject to high angles of ambient light 133 as well as scattered excitation light 129.

As illustrated in FIG. 5, at 0° angle of incidence (AOI), conventional dichroic filters 111 and 113 accomplish the ideal filtering scheme. The dark blue line 501 represents the ideal passband for the reference filter 113 placed over the second photodetector 112, and the purple line 502 represents the ideal passband for the signal filter 111 placed over the first photodetector 110. The red line 503 represents the excitation light 129, which peaks at 378 nm, and the high and low emission of the chemistry is shown by the light blue line 504 and orange line 505, respectfully. As shown in FIG. 5, the highest wavelengths of the excitation light 108 may creep into the passband of the signal channel filter 111 at very low levels of throughput. Accordingly, in the ideal situation shown in FIG. 5, a negligible amount of excitation light 129 relative to the total amount of the excitation light 129 may pass into the signal channel photodetector 110. Achieving relatively high signal (i.e., desired light) to noise (i.e., undesired light) ratios provides the purest signal possible, but the conventional dichroic filters 111 and 113 do not perfectly filter light.

Figure 6:
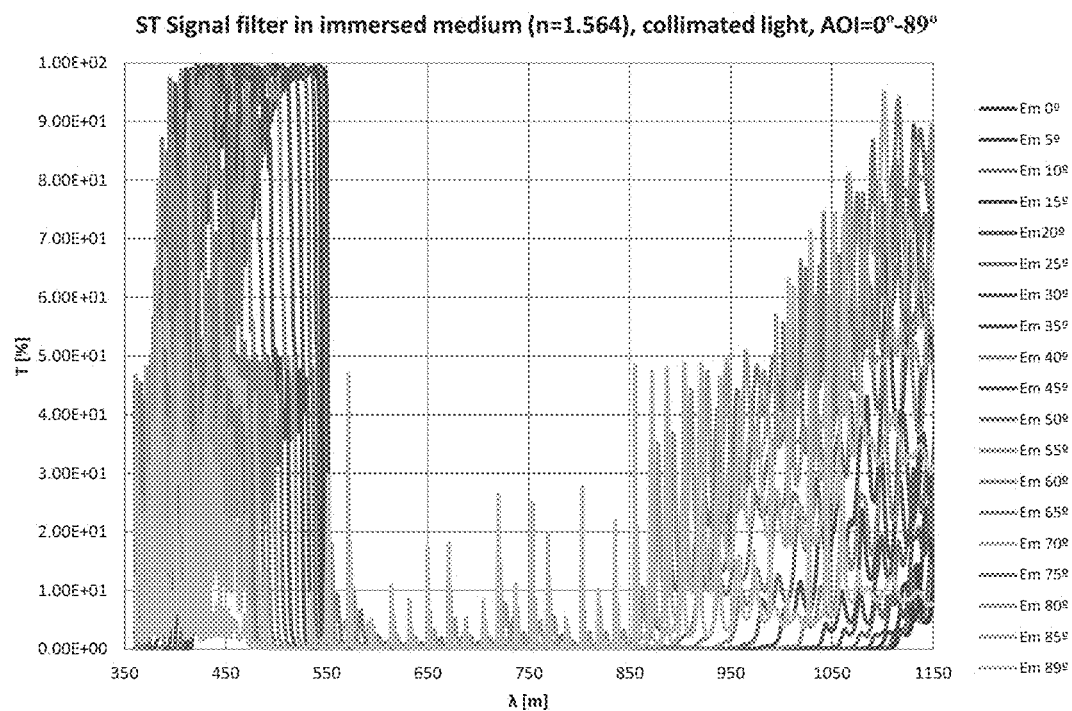
FIG. 6 is a graph illustrating the transmission percentage of a signal channel dichroic band pass filter at different angles of incidence.
Figure 7:
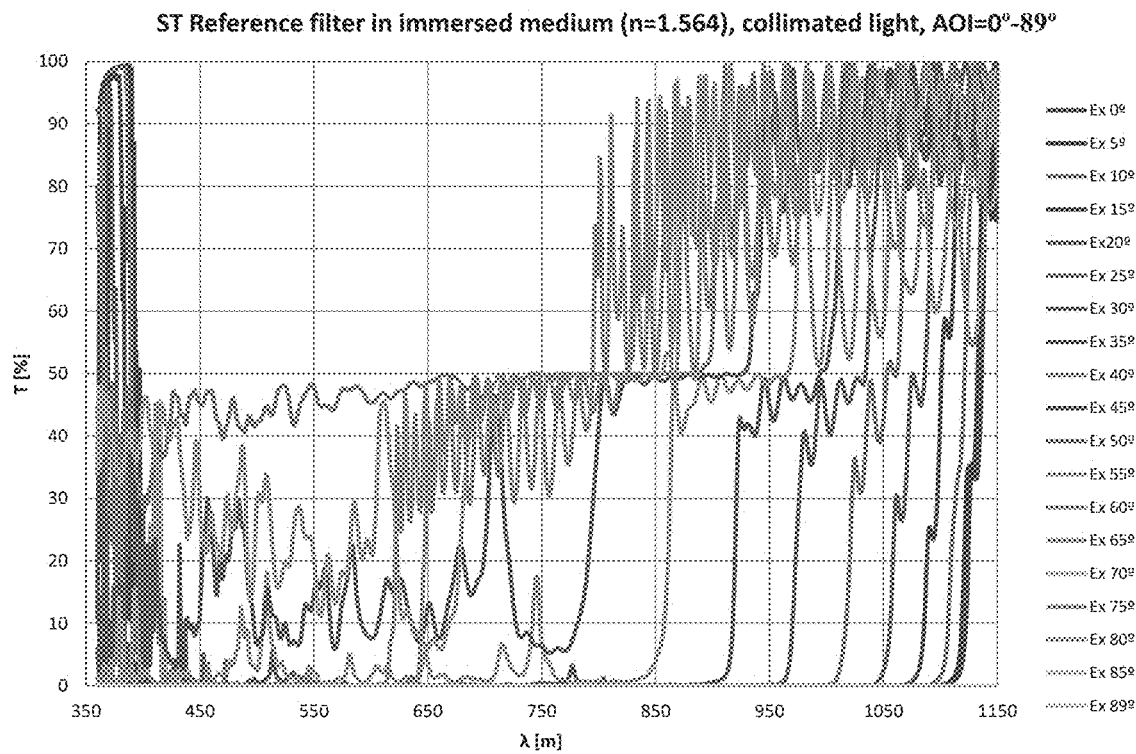
FIG. 7 is a graph illustrating the transmission percentage of a reference channel dichroic band pass filter at different angles of incidence.

FIG. 6 is a graph illustrating the transmission percentage of the conventional signal channel dichroic band pass filter 111 at different angles of incidence. FIG. 7 is a graph illustrating the transmission percentage of the conventional reference channel dichroic band pass filter 113 at different angles of incidence. FIGS. 6 and 7 show the quality of the conventional signal and reference channel dichroic filters 111 and 113 decaying as a function of angle of incidence. When this happens across the light spectrum, the conventional dichroic filters 111 and 113 have a much lower signal to noise ratio, and, therefore, the conventional filters 111 and 113 are not performing as intended. As a result, complex algorithms may be required to obtain useful signal.

Figure 10:
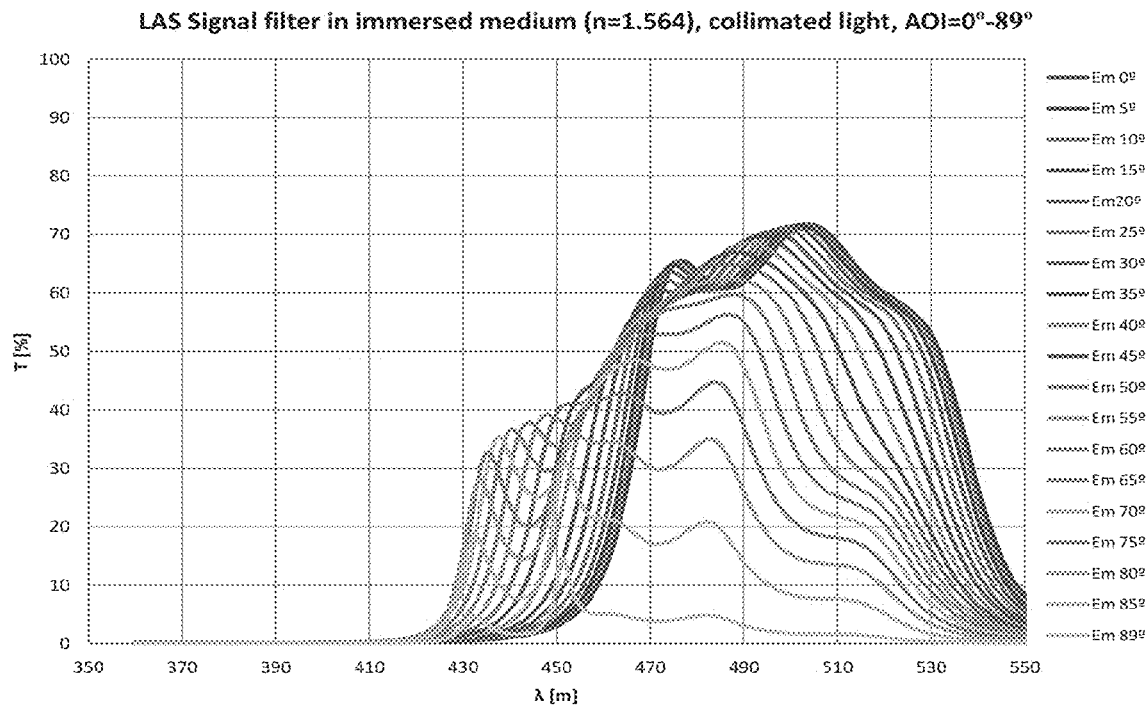
FIG. 10 is a graph illustrating the transmission percentage of a signal channel low angle sensitive filter embodying aspects of the present invention at different angles of incidence.
Figure 11:
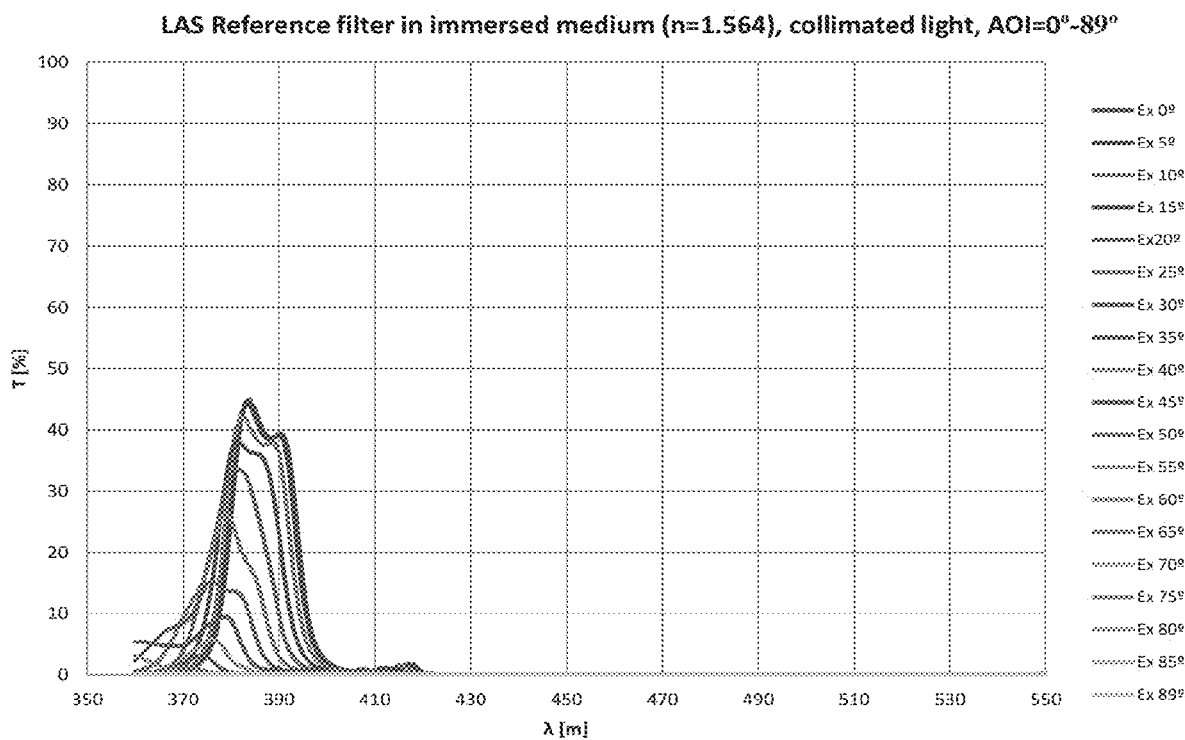
FIG. 11 is a graph illustrating the transmission percentage of a reference channel low angle sensitive filter embodying aspects of the present invention at different angles of incidence.

FIG. 10 is a graph illustrating the transmission percentage of one embodiment of the signal channel LAS optical filter 937 at different angles of incidence, in accordance with aspects of the invention. FIG. 11 is a graph illustrating the transmission percentage of one embodiment of the reference channel LAS optical filter 939 at different angles of incidence, in accordance with aspects of the invention. FIGS. 10 and 11 show that the downward shift in the passband of the LAS optical filters 937 and 939 as the angle of incidence increases is greatly reduced relative to the downward shift in the passband of the conventional dichroic filters 111 and 113 (see FIGS. 6 and 7). In some embodiments, as shown in FIGS. 10 and 11, the downward shift in the passband of the LAS optical filters may be 20 nm or less. In some embodiments, as shown in FIGS. 10 and 11, the transmission efficiency of the LAS optical filters is greatly reduced as the angle of incidence increases.

In some embodiments, the analyte indicator 106 may be positioned relative to the signal channel LAS optical filter 937 and/or the reference channel LAS optical filter 939 such that at least a portion of the emission light reaches the signal channel LAS optical filter 937 and/or the reference channel LAS optical filter 939 as low angle of incidence light. In some non-limiting embodiments, the low angle of incidence light may have, for example, an angle of incidence less than or equal to 25 degrees, an angle of incidence less than or equal to 20 degrees, an angle of incidence less than or equal to 15 degrees, an angle of incidence less than or equal to 10 degrees, or an angle of incidence less than or equal to 5 degrees. In some embodiments, the angle of incidence may be the angle of the optical axis relative to a line perpendicular to a receiving surface of the LAS optical filter. Accordingly, light would have an angle of incidence is 0° if light has an optical axis that is perpendicular to the receiving surface of the LAS optical filter, and light would have an angle of incidence of 90° if the light has an optical axis that is parallel to the receiving surface of the LAS optical filter.

Figure 8A:
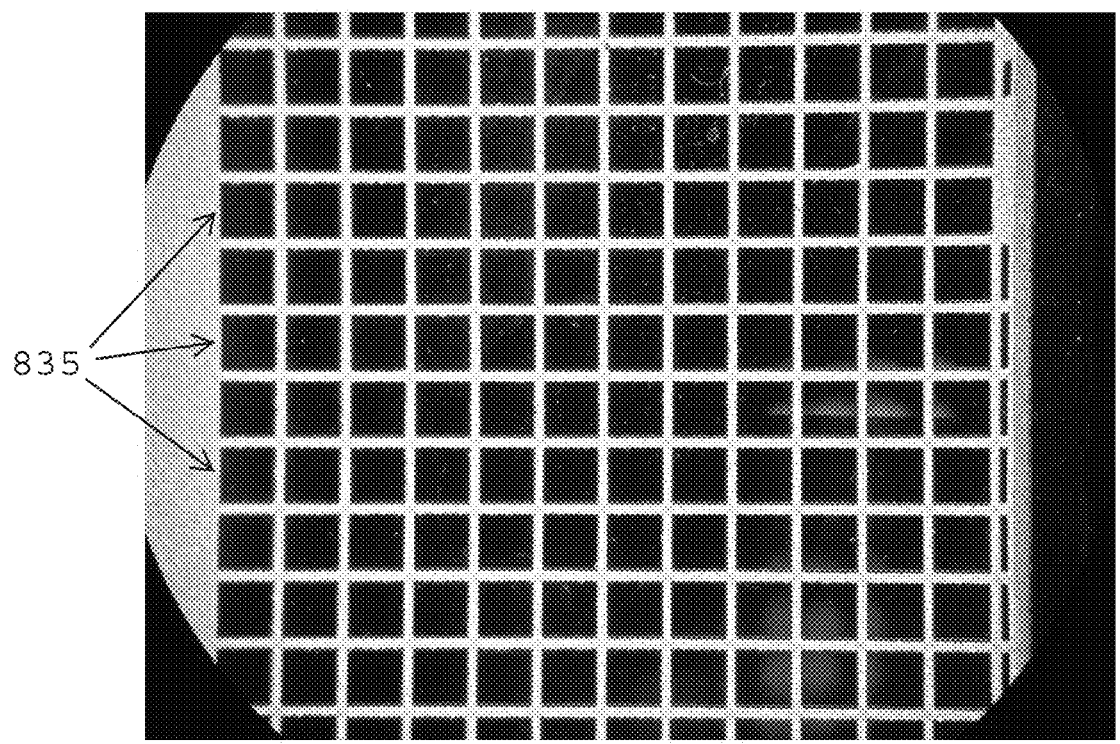
FIGS. 8A-8C illustrate pre-diced glass slides coated with dichroic filters.
Figure 8B:
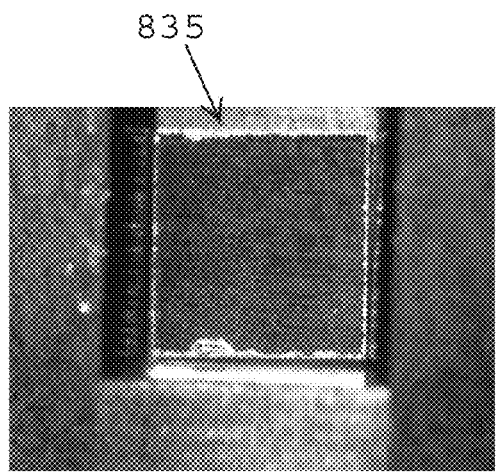
Figure 8C:
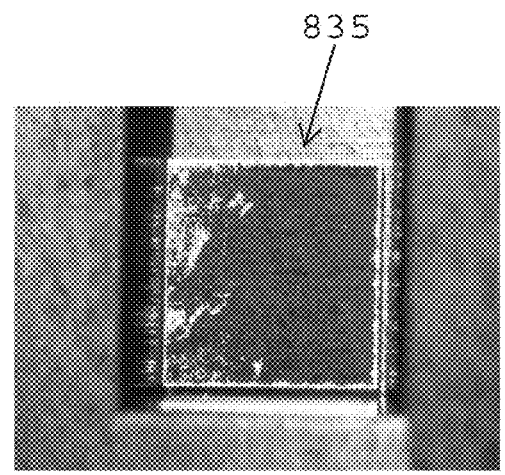

In addition, the first and second photodetectors 110 and 112 in the small scale optical system of the sensor 100 have light receiving areas of 1 mm², and, as a result, application of the filters may be difficult. As illustrated in FIG. 8A, the conventional filters 111 and 113 are assembled by dicing glass slides 835 and coating the glass with the filters. The filter-coated glass slides 835 are then attached above the first and second photodetectors 110 and 112. However, this may be a tedious process with a lot of handling and chances for defects. As illustrated in FIGS. 8B and 8C, dicing the glass may result in chip outs along the edges of the glass slides 835, which may allow for areas above the photodiodes to not be filtered. Also, the attachment and alignment of such small pieces of glass is may be expensive, and achievement of consistency may be difficult.

Accordingly, in some non-limiting embodiments, the one or more LAS optical filters may be deposited directly on the one or more photodetectors (e.g., via magnetron sputter coating), and the directly deposited LAS optical filters may have improved quality and/or attachment relative to filters deposited on glass slides. In some non-limiting embodiments where the one or more photodetectors are fabricated in a semiconductor substrate, the one or more LAS optical filters are deposited directly on the semiconductor substrate. Directly coating the wafer is a lab on a chip assembly process that moves towards complete wafer level processing by having a fully integrated optical system on an integrated circuit.

Figure 12:
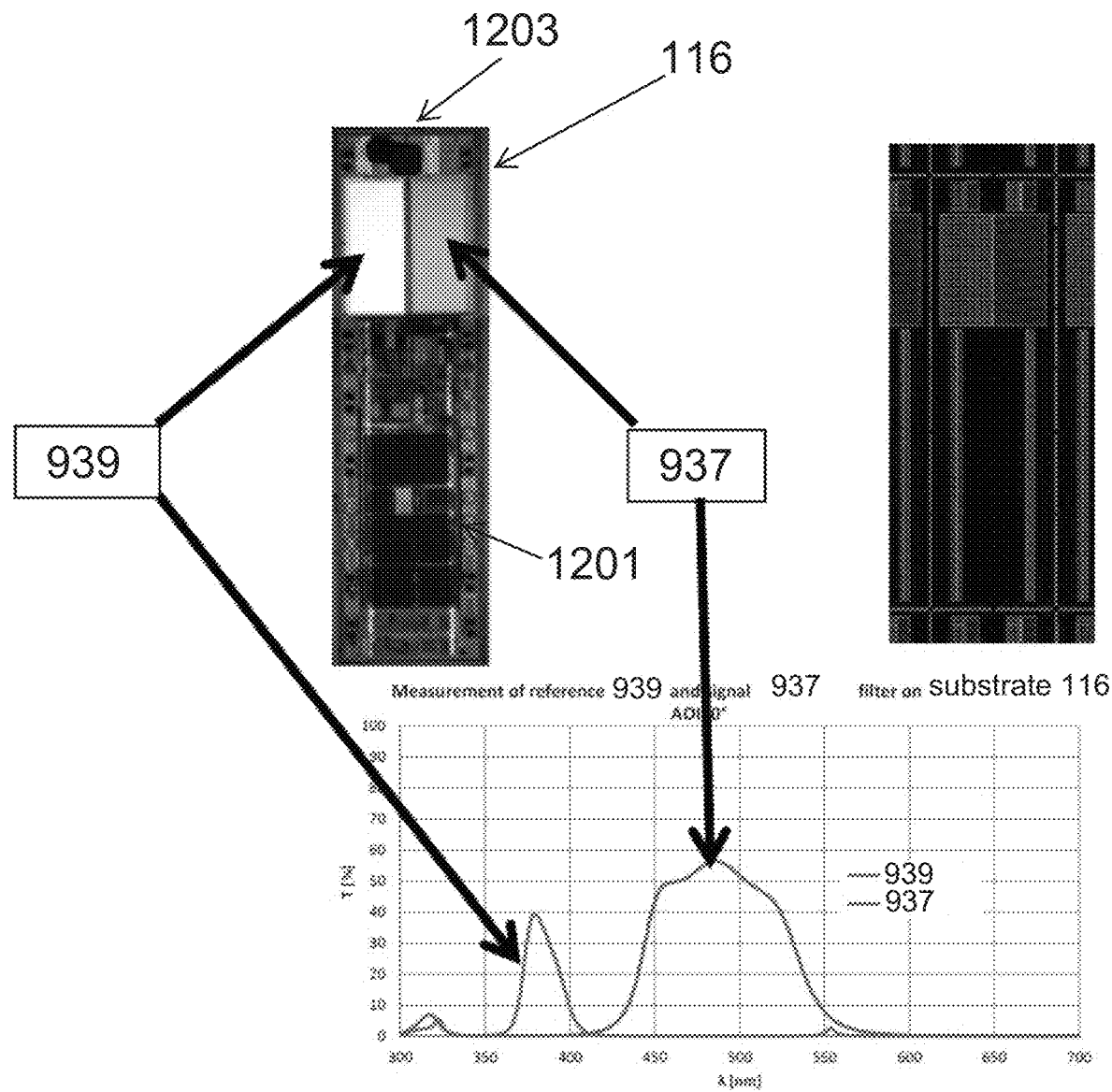
FIG. 12 is a schematic view of low angle sensitivity (LAS) optical filters on the substrate of a sensor embodying aspects of the present invention and a graph illustrating the transmission percentage of the LAS optical filters at different wavelengths.

FIG. 12 illustrates an embodiment in which the substrate 116 is a semiconductor substrate, the photodetectors 110 and 112 are fabricated on the semiconductor substrate, and the LAS optical filters 937 and 939 are coated on the photodetectors 110 and 112, respectively. In some embodiments, as shown in FIG. 12, the substrate 116 may include a mount 1203 for the light source 108 and additional circuitry 1201, which may be fabricated in and/or mounted on the substrate 116. FIG. 12 also includes a graph illustrating the transmission percentage of the LAS optical filters 937 and 939 at different wavelengths and an angle of incidence of 0°.

In some embodiments, the signal channel LAS optical filter 937 has a transmission efficiency that is sufficient for detection of modulation in the emission light 131 due to presence and/or concentration of analyte in the medium into which the sensor is inserted (see the high and low emission of the analyte indicator chemistry shown by the light blue line 504 and orange line 505, respectfully, of FIG. 5). In some embodiments, the LAS optical filters may have low sensitivity to high angle of incidence light. That is, in some embodiments, the LAS optical filters may pass only small percentage of high angle of incidence light. Accordingly, in some embodiments, the sensor 900 having LAS optical filters 937 and 939 may be a highly miniaturized dual channel precision fixed fluorimeter. In some non-limiting embodiments, the sensor 900 may have an excitation wavelength at approximately 380 nm, an emission wavelength range beginning at 390 nm, and the ability to separately isolate and detect the excitation light and emission light (via the photodectors and LAS optical filters) with a very low signal to noise ratio. In some non-limiting embodiments, the LAS optical filters may be accurate filters with turn on and turn offs of a few nanometers in a narrowband with little to no angle of incidence sensitivity and may allow for a level of detection not achieved by other sensors optical systems.

In one non-limiting embodiment, the signal channel LAS optical filter 937 and/or reference channel LAS optical filter 939 may have one or more of the following specifications.

| LAS Optical Filter | Wavelength | % Transmission @ 0° AOI | Wavelength | % Transmission @ 75° AOI |
|---|---|---|---|---|
| signal channel LAS optical filter 937 | 300 nm-410 nm | Tave <2% | 300 nm-395 nm | Tave <1% |
| | 350 nm-410 nm | Tave <0.5% | 350 nm-395 nm | Tave <0.5% |
| | 350 nm-410 nm | Tmax <2% | 350 nm-395 nm | Tmax <2% |
| | 455 nm-525 nm | Tave >47% | 420 nm-510 nm | Tave >16% |
| | 600 nm-1100 nm | Tave <0.1% | 600 nm-1100 nm | Tave <0.1% |
| | 600 nm-1100 nm | Tmax <1% | 600 nm-1100 nm | Tmax <1% |
| | Rel 50% T | 443.5 nm +/− 5 nm | Rel 50% | 410 nm +/− 5 nm |
| | Rel 50%_T | 532.0 nm +/− 6 nm | Rel 50 | 518.5 nm +/− 6 nm |
| reference channel LAS optical filter 939 | 300 nm-350 nm | Tave <2% | 300 nm-340 nm | Tave <2% |
| | 376 nm-386 nm | Tave >33% | 350 nm-374 nm | Tave >4% |
| | 415 nm-490 nm | Tave <0.1% | 415 nm-490 nm | Tave <0.1% |
| | 415 nm-1100 nm | Tmax <4% | 415 nm-1100 nm | Tmax <3% |
| | 415 nm-1100 nm | Tave <0.5% | 415 nm-1100 nm | Tave <0.5% |
| | Rel 50% T | 372 nm +/− 4 nm | Rel 50% | 346 nm +/− 4 nm |
| | Rel 50% T | 394 nm +/− 4.5 nm | Rel 50% | 379 nm +/− 4 nm |

Embodiments of the present invention have been fully described above with reference to the drawing figures. Although the invention has been described based upon these preferred embodiments, it would be apparent to those of skill in the art that certain modifications, variations, and alternative constructions could be made to the described embodiments within the spirit and scope of the invention.

What is claimed is:

1. An apparatus comprising:
a first low angle sensitive (LAS) optical filter comprising layers configured to:
prevent light having a wavelength outside a first band pass region from reaching a first photodetector,
permit light reaching the first LAS optical filter at a first angle of incidence and having a wavelength within the first band pass region to pass to the first photodetector at a first transmission percentage, and
permit light reaching the first LAS optical filter at a second angle of incidence higher than the first angle of incidence and having a wavelength within the first band pass region to pass to the first photodetector at a second transmission percentage, wherein the second angle of incidence is greater than or equal to 40 degrees, and the second transmission percentage is lower than the first transmission percentage and greater than zero; and
a second LAS optical filter comprising layers configured to:
prevent light having a wavelength outside a second band pass region from reaching a second photodetector, wherein the second band pass region is different than the first band pass region,
permit light reaching the second LAS optical filter at the first angle of incidence and having a wavelength within the second band pass region to pass to the second photodetector at a third transmission percentage, and
permit light reaching the second LAS optical filter at the second angle of incidence and having a wavelength within the second band pass region to pass to the second photodetector at a fourth transmission percentage, wherein the fourth transmission percentage is lower than the third transmission percentage and greater than zero.

2. The apparatus of claim 1, wherein the first LAS optical filter is a plasmonic nanostructured filter.

3. The apparatus of claim 1, wherein the layers of the first LAS optical filter comprise layers of metal and oxides, and the layers of the second LAS optical filter comprise layers of metal and oxides.

4. The apparatus of claim 3, wherein the layers of metal and oxides of the first LAS optical filter have a thickness configured to pass light within the first band pass region.

5. The apparatus of claim 3, wherein the layers of metal and oxides of the first LAS optical filter are deposited on the first photodetector.

6. The apparatus of claim 5, wherein the layers of metal and oxides of the first LAS optical filter are deposited on the first photodetector by magnetron sputter coating.

7. The apparatus of claim 3, further comprising a glass slide positioned on the first photodetector, wherein the layers of metal and oxides of the first LAS optical filter are deposited on the glass slide.

8. The apparatus of claim 7, wherein the glass slide comprises an exit surface opposite a receiving surface, and the layers of metal and oxides of the first LAS optical filter are deposited on the exit surface of the glass slide.

9. The apparatus of claim 1, wherein the first bandpass region shifts by 20 nm or less as the angle of incidence of light received by the first LAS optical filter increases from 0 degrees to 89 degrees.

10. The apparatus of claim 1, wherein the first angle of incidence is less than or equal to 25 degrees.

11. The apparatus of claim 1, wherein the first angle of incidence is less than or equal to 20 degrees.

12. The apparatus of claim 1, wherein the first angle of incidence is less than or equal to 15 degrees.

13. The apparatus of claim 1, wherein the first angle of incidence is less than or equal to 10 degrees.

14. The apparatus of claim 1, wherein the first angle of incidence is less than or equal to 5 degrees.

15. The apparatus of claim 1, wherein the first angle of incidence is 0 degrees, and the first transmission percentage is less than 90%.

16. The apparatus of claim 1, wherein the first angle of incidence is 0 degrees, and the first transmission percentage is less than 80%.

17. The apparatus of claim 1, wherein the first angle of incidence is 0 degrees, and the third transmission percentage is less than 80%.

18. The apparatus of claim 1, wherein the second angle of incidence is equal to 40 degrees.

19. The apparatus of claim 1, wherein the second angle of incidence is equal to 45 degrees.

20. A method of using an apparatus comprising a first low angle sensitive (LAS) optical filter comprising layers and a second LAS optical filter comprising layers, the method comprising:

receiving, by the first LAS optical filter, first light;

preventing, by the layers of the first LAS optical filter, light of the received first light having a wavelength outside a first band pass region from reaching a first photodetector;

permitting, by the layers of the first LAS optical filter, light of the received first light having a first angle of incidence and a wavelength within the first band pass region to reach the first photodetector at a first transmission percentage;

permitting, by the layers of the first LAS optical filter, light of the received first light having a second angle of incidence higher than the first angle of incidence and a wavelength within the first band pass region to reach the first photodetector at a second transmission percentage, wherein the second angle of incidence is greater than or equal to 40 degrees, and the second transmission percentage is lower than the first transmission percentage and greater than zero;

receiving, by the second LAS optical filter, second light;

preventing, by the layers of the second LAS optical filter, light of the received second light having a wavelength outside a second band pass region from reaching a second photodetector, wherein the second bandpass region that is different than the first bandpass region;

permitting, by the layers of the second LAS optical filter, light of the received second light having the first angle of incidence and a wavelength within the second band pass region to reach the second photodetector at a third transmission percentage;

permitting, by the layers of the second LAS optical filter, light of the received second light having the second angle of incidence and a wavelength within the second band pass region to reach the second photodetector at a fourth transmission percentage, wherein the fourth transmission percentage is lower than the third transmission percentage and greater than zero.

21. The method of claim 20, wherein the layers of the first LAS optical filter comprise layers of metal and oxides, and the layers of the second LAS optical filter comprise layers of metal and oxides.

22. The method of claim 21, wherein the layers of metal and oxides of the first LAS optical filter have a thickness configured to pass light within the first band pass region.

23. The method of claim 20, wherein the first bandpass region shifts by 20 nm or less as the angle of incidence of light received by the first LAS optical filter increases from 0 degrees to 89 degrees.

24. The method of claim 20, wherein the first angle of incidence is less than or equal to 10 degrees.

25. The method of claim 20, wherein the first angle of incidence is less than or equal to 5 degrees.

26. The method of claim 20, wherein the second angle of incidence is equal to 40 degrees.

27. The method of claim 20, wherein the second angle of incidence is equal to 45 degrees.

28. The apparatus of claim 1, wherein the first angle of incidence is 0 degrees, and the third transmission percentage is less than 50%.

* * * * *